United States Patent [19]

Skorianetz et al.

[11] 4,438,023
[45] Mar. 20, 1984

[54] OXYGENATED TRICYCLIC DERIVATIVES OF NORBORNANE AND USE OF SAME AS PERFUMING INGREDIENTS

[75] Inventors: Werner Skorianetz, Dardagny; Günther Ohloff, Bernex, both of Switzerland

[73] Assignee: Firmenich SA, Geneva, Switzerland

[21] Appl. No.: 366,552

[22] Filed: Apr. 8, 1982

[30] Foreign Application Priority Data

May 21, 1981 [CH] Switzerland .......................... 3315/81

[51] Int. Cl.³ ...................... C11B 9/00; C07D 311/78
[52] U.S. Cl. ................................ 252/522 R; 549/386
[58] Field of Search ...................... 252/522 R; 549/386

[56] References Cited

U.S. PATENT DOCUMENTS 4,159,258  6/1979  Ohloff et al. .................. 252/522 A Primary Examiner—Nicky Chan
Attorney, Agent, or Firm—Pennie & Edmonds

[57] ABSTRACT

Oxygen containing tricyclic derivatives of norbornane of formula

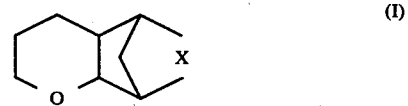

(I)

wherein symbol X represents a divalent radical of formula

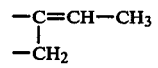

possess valuable organoleptic properties and consequently can be used as perfuming ingredients.

7 Claims, No Drawings

OXYGENATED TRICYCLIC DERIVATIVES OF NORBORNANE AND USE OF SAME AS PERFUMING INGREDIENTS

BRIEF SUMMARY OF THE INVENTION

The present invention relates to the field of perfumery, more particularly it provides novel oxygenated derivatives of norbornane of formula

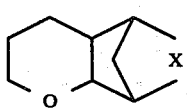

wherein symbol X represents a divalent radical of formula

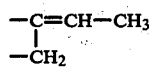

Compounds of formula (I) possess useful olfactive properties. It is an object of the present invention to provide a process to enhance, modify or improve the odor properties of perfumes and perfumed products, which process consists in adding thereto an odorous effective amount of a compound of formula (I).

The instant invention also provides a perfume composition containing as perfuming effective ingredient a compound of formula (I).

This invention relates moreover to a process for the preparation of compounds of formula (I), which consists in reducing by catalytic hydrogenation a compound of formula

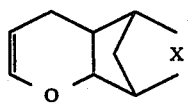

wherein symbol X represents a divalent radical of formula

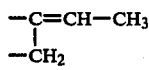

BACKGROUND OF THE INVENTION

Among the compounds possessing a chemical structure analogous to that of the compounds of formula (I), one may cite the tricyclic lactone derivatives of norbornane of formula

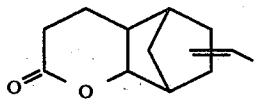

These compounds are disclosed in U.S. Pat. No. 4,159,258. They are characterized by an odor note of green, fresh, herbaceous, slightly fatty and occasionally spicy type.

Though the novel compounds of the invention develops a scent which presents an analogy with some of the characters of the odor feature of the cited prior known lactones, their fragrance is more aromatic and slightly pungent. They possess moreover a green and herbaceous tonality reminiscent of the flowers of elder-tree or honeysuckle. The use of these compounds greatly enriches the perfumer's choice among the synthetic chemicals he has to his disposal for his creation activity. Compounds (I) find a utility for the preparation of luxury perfumes as well as for the manufacture of cosmetics, soaps, detergents or household products.

PREFERRED EMBODIMENTS OF THE INVENTION

As usual in the art, compounds (I) can be used in accordance with the invention in a wide range of proportions. Concentrations of the order of 0.1% by weight, based on the total weight of the perfumed product, can already produce a marked effect. However, in most of the applications under consideration, these values vary in between 1 and 20%, depending on the specific effect it is desired to achieve and on the nature of the perfumed products. These values depend also on the specific coingredients, solvents or supports of the given composition into which compounds (I) may have been incorporated. The compounds of the invention can be prepared by a process which consists in reducing by a catalytic hydrogenation the corresponding unsaturated compounds of formula (II), these latter being obtained by the addition of acrolein to norbornene according to the following reaction scheme:

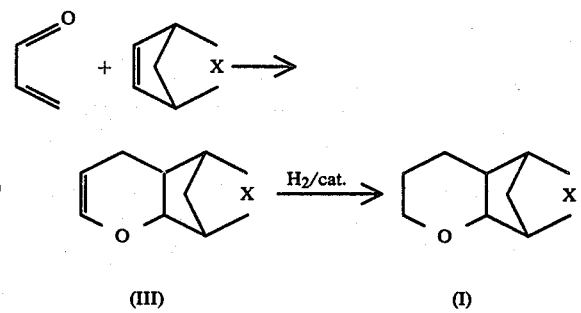

Starting materials (II), used for the preparation of the compounds of the invention, can be obtained in accordance with the process described in U.S. Pat. No. 4,159,258 via a reaction which formally constitutes a cyclo-addition of Diels-Alder type at a temperature ranging from about 150° to 250° C. and at a pressure of about 15 to 150 atm. Compounds (II) thus obtained can occur under the form of a mixture of isomers whose respective structure is characterized by the presence of an ethylidenyl radical in position 9 or 10 of the ring. For all practical purposes, these mixtures can be used as directly obtained in the above described process. Their catalytic hydrogenation in the presence of a metal catalyst, such as for instance palladium on charcoal, yields, after absorption of one equivalent of hydrogen, the corresponding mixtures of compounds (I). Formula (I) is deemed to define not only the positional isomers with respect to the ethylidenyl radical but also the different stereoisomers which arise as a result of the orientation of the ethylidenyl double bond and the hydrogen atoms at one of the bridgehead pair. This situation can be visualized as follows:

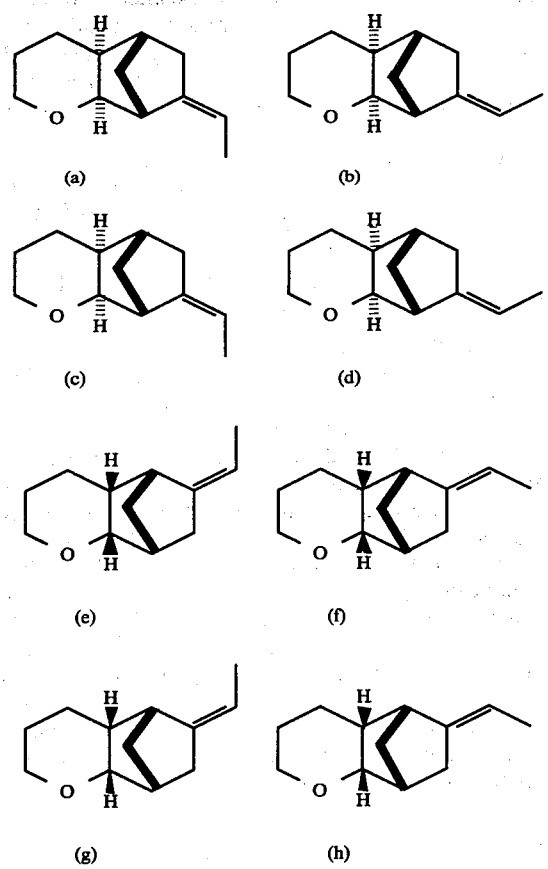

(a) (b) (c) (d) (e) (f) (g) (h)

By the process described above, one obtains an isomeric mixture eminently consisting of the pair of exo type a/b and e/f in the proportions of about 45.5/13 and 32.5/9, respectively.

The invention is illustrated by the following examples wherein the temperatures are indicated in degrees centigrade and the abbreviations have the meaning common in the art.

EXAMPLE 1

Preparation of compounds of formula (I)

53 g (0.3 M) of the product obtained by the reaction of ethylidene-norbornene with acrolein [see Example 1 of U.S. Pat. No. 4,159,258] were dissolved in 250 ml of methanol and the solution was subjected to hydrogenation in the presence of 3 g palladium at 5% charcoal. The reaction was stopped after adsorption of one equivalent of hydrogen (7.2 l), whereupon the mixture was filtered and the clear filtrate was distilled over a bulb-apparatus (130° bath temperature/0.01 Torr). 52.3 g (yield 98%) of the desired product were thus isolated. Its analytical characters were the following:

IR: 3040, 2920, 1670, 1460, 1375, 1265, 1190, 1080, 1040, 989, 942, 906, 805, 642 cm$^{-1}$;

MS: M$^+$=178(50); m/e: 163(17), 149(15), 135(9.4), 119(27), 106(16), 94(77), 93(100), 79(87), 67(18), 55(27), 41(42);

NMR (360 MHz): signals at 2.19; 2.60; 2.62; 2.93 δ ppm; $^{13}$C: 14.04; 79.29; 114.97; 141.48 14.62; 78.12; 115.75; 140.51 13.71; 79.81; 110.87; 145.12 14.43; 79.90; 111.59; 144.3 δ ppm.

A spectral analysis has enabled us to assign to the thus obtained mixture the following composition:

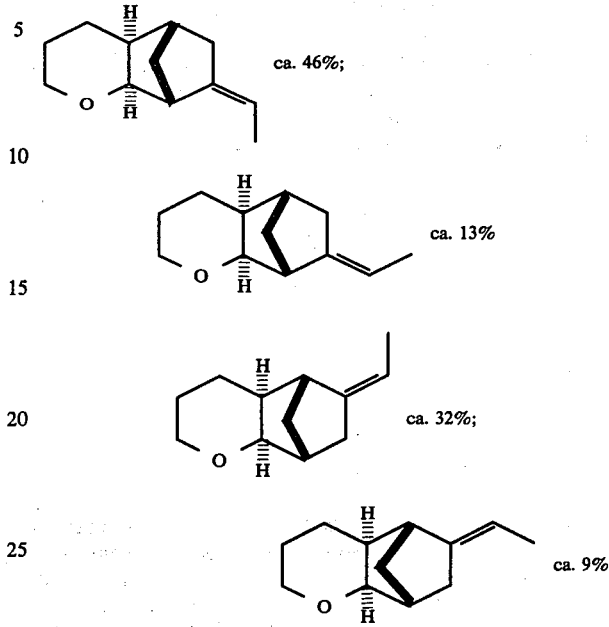

ca. 46%;
ca. 13%
ca. 32%;
ca. 9%

EXAMPLE 2

Perfume for shampoos

A perfume base composition destined to perfume shampoos was prepared by mixing the following ingredients (parts by weight):

| | |
|---|---|
| Trimethyl-hexyl acetate | 200 |
| Geranylacetone | 100 |
| Benzyl salicylate | 80 |
| Hexylcinnamic aldehyde | 80 |
| 1,3-Dimethyl-but-3-en-1-yl isobutyrate | 80 |
| p-tert-Butyl-α-methyl hydrocinnamaldehyde | 60 |
| Phenylethyl alcohol | 60 |
| α-Isomethylionone | 40 |
| Ylang-ylang oil | 40 |
| 4-Isopropyl-cyclohexylmethanol[1] | 40 |
| Hydratropic alcohol | 40 |
| Anisaldehyde 10%* | 30 |
| Anisic alcohol | 20 |
| Allyl phenoxyacetate | 10 |
| Methyl geraniate | 10 |
| Trichloro-methyl-phenyl carbinyl acetate (crystallized) | 10 |
| α-Damascone 10%* | 10 |
| Exaltex ® 10%*[2] | 10 |
| Phenoxyethyl isobutyrate | 10 |
| Trimethyl-cyclohexen-carboxyaldehyde 10%* | 10 |
| Total | 940 |

*in diethyl phthalate
[1]U.S. Pat. No. 3,993,604; Mayol ® (origin: Firmenich SA)
[2]Cyclopentadecanolide The thus obtained base composition possessed a fresh-flowery character. By adding to 94 g of the above base, 6 g of the isomeric mixture of 3-oxa-9-ethylidene-tricyclo[6.2.1.0$^{2,7}$]undecane and 3-oxa-10-ethylidene-tricyclo[6.2.1.0$^{2,7}$]undecane obtained according to Example 1, one obtains a novel composition possessing an original and clinging note of elder flowers.

What we claim is:

1. Compounds of formula

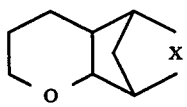 (I)

wherein symbol X represents a divalent radical of formula $$\begin{array}{c}-C=CH-CH_3\\|\\-CH_2\end{array}$$

2. 3-Oxa-9-ethylidene-tricyclo[6.2.1.0$^{2,7}$]undecane.

3. 3-Oxa-10-ethylidene-tricyclo[6.2.1.0$^{2,7}$]undecane.

4. Compounds according to claim 2 under the form of one of the isomers of formulae

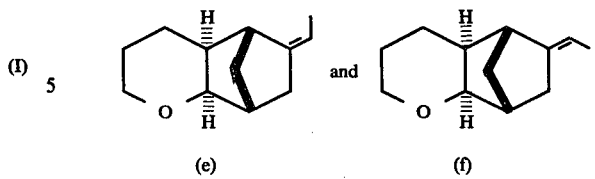

(e)   (f)

5. Compounds according to claim 3 under the form of one of the isomers of formulae

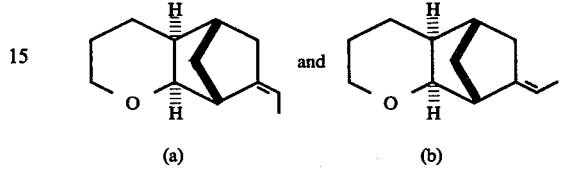

(a)   (b)

6. Process to enhance, modify or improve the odor properties of perfumes and perfumed products, which consists in adding thereto an odorous effective amount of a compound of formula (I) as set forth in claim 1.

7. A perfuming composition containing as perfuming ingredient 0.1% to 20% of a compound of formula (I) as set forth in claim 1.

* * * * *